(12) United States Patent
Huenink et al.

(10) Patent No.: US 11,945,515 B2
(45) Date of Patent: Apr. 2, 2024

(54) UTILITY VEHICLE

(71) Applicant: DEERE & COMPANY, Moline, IL (US)

(72) Inventors: Brian M. Huenink, Cedar Grove, WI (US); Gregory O. Mcconoughey, Le Claire, IA (US)

(73) Assignee: Deere & Company, Moline, IL (US)

( * ) Notice: Subject to any disclaimer, the term of this patent is extended or adjusted under 35 U.S.C. 154(b) by 375 days.

(21) Appl. No.: 17/307,692

(22) Filed: May 4, 2021

(65) Prior Publication Data

US 2022/0063737 A1 Mar. 3, 2022

Related U.S. Application Data

(60) Provisional application No. 63/072,760, filed on Aug. 31, 2020.

(51) Int. Cl.
| | | |
|---|---|---|
| *B60R 1/12* | (2006.01) | |
| *A61B 5/00* | (2006.01) | |
| *B62D 33/06* | (2006.01) | |
| *B62D 33/073* | (2006.01) | |

(52) U.S. Cl.
CPC .......... *B62D 33/073* (2013.01); *A61B 5/6893* (2013.01); *B60R 1/12* (2013.01); *B62D 33/0625* (2013.01)

(58) Field of Classification Search
CPC .............................. B60R 1/12; B62D 33/0617
See application file for complete search history.

(56) References Cited

U.S. PATENT DOCUMENTS

| | | | |
|---|---|---|---|
| 4,463,426 A | | 7/1984 | Caddick et al. |
| 4,464,016 A | * | 8/1984 | Weber ................... B60R 1/0612 359/877 |
| 4,689,537 A | | 8/1987 | Mizuta et al. |
| 5,196,965 A | * | 3/1993 | Lang ....................... B60R 1/025 359/876 |
| 5,306,953 A | * | 4/1994 | Weiner ................. G01S 15/931 359/604 |

(Continued)

FOREIGN PATENT DOCUMENTS

| | | |
|---|---|---|
| DE | 19919216 C2 | 10/2001 |
| DE | 102004016315 A1 | 10/2005 |

(Continued)

*Primary Examiner* — Hilary L Gutman
(74) *Attorney, Agent, or Firm* — TUCKER ELLIS LLP; Heather M. Barnes; Michael G. Craig

(57) ABSTRACT

A utility vehicle including an operator cab, an operator support positioned within the operator cab and movable relative to the operator cab, a mirror positioned outwardly relative to the operator cab, and a control system including a controller in communication with the operator support and the mirror. The controller is configured to select a first setting from a first plurality of settings and a second setting from a second plurality of settings. Each setting of the first plurality of settings corresponding to one of a plurality of operations performed by the vehicle and each setting of the second plurality of settings corresponding to one of a plurality of operators. The controller is configured to adjust at least a position of the support relative to the cab and a position of the mirror relative to the operator cab based on the first setting and the second setting.

20 Claims, 4 Drawing Sheets

(56) References Cited

U.S. PATENT DOCUMENTS

| | | | |
|---|---|---|---|
| 6,061,617 A * | 5/2000 | Berger | E02F 3/438 |
| | | | 701/34.2 |
| 7,597,398 B2 | 10/2009 | Lindsay | |
| 7,669,928 B2 | 3/2010 | Snyder | |
| 7,681,949 B2 | 3/2010 | Nathan et al. | |
| 7,684,949 B2 | 3/2010 | Koerner | |
| 7,708,343 B2 | 5/2010 | Kayumi et al. | |
| 7,819,474 B2 | 10/2010 | Gloriosa | |
| 9,010,946 B1 * | 4/2015 | Setnor | B60R 1/025 |
| | | | 359/843 |
| 9,321,373 B2 | 4/2016 | Sakata et al. | |
| 9,848,814 B2 | 12/2017 | Benson et al. | |
| 10,773,624 B2 | 9/2020 | Morrow | |
| 2005/0006955 A1 * | 1/2005 | Olijnyk | B60R 1/07 |
| | | | 307/10.1 |
| 2010/0017071 A1 * | 1/2010 | Ryu | B60R 1/02 |
| | | | 701/49 |
| 2014/0172127 A1 * | 6/2014 | Johnson | G05B 19/409 |
| | | | 700/65 |
| 2017/0147958 A1 | 5/2017 | Hatfield et al. | |
| 2017/0297581 A1 | 10/2017 | Hatfield et al. | |
| 2018/0264974 A1 * | 9/2018 | Ramachandran | B60N 2/0232 |
| 2020/0223312 A1 * | 7/2020 | Heitsman | B60K 28/066 |
| 2021/0016686 A1 * | 1/2021 | Yetukuri | B60N 2/5621 |
| 2022/0224963 A1 * | 7/2022 | Herz | G06Q 50/30 |

FOREIGN PATENT DOCUMENTS

| | | | | |
|---|---|---|---|---|
| DE | 102008004121 A1 | | 7/2009 | |
| DE | 102013211721 A1 | | 12/2013 | |
| DE | 102012216869 A1 | * | 3/2014 | B60R 21/015 |
| DE | 102015219461 A1 | | 4/2017 | |
| DE | 102018007365 A1 | | 1/2019 | |
| KR | 1019970036515 A | | 7/1997 | |
| WO | WO-2006119857 A1 | * | 11/2006 | B60N 2/0248 |

* cited by examiner

UTILITY VEHICLE

CROSS-REFERENCE TO RELATED APPLICATIONS

This application claims priority to U.S. Provisional Patent Application No. 63/072,760 filed on Aug. 31, 2020, the contents of which is incorporated herein by reference.

FIELD

The present subject matter relates to a utility vehicle operated by different operators for different operations. Specifically, the present subject matter relates to a utility vehicle that manipulates the position of an operator support (e.g., a chair), one or more mirrors, and in some applications aspects related to certain implements based on the individual operator and operation performed by the utility vehicle.

SUMMARY

In one embodiment, a utility vehicle includes a chassis, a prime mover supported by the chassis, an operator cab supported by the chassis, an operator support positioned within the operator cab and movable relative to the operator cab, a mirror positioned outwardly relative to the operator cab and movable relative to the operator cab, and a control system including a controller in communication with the operator support and the mirror. The controller is configured to select a first setting from a first plurality of settings and a second setting from a second plurality of settings. Each setting of the first plurality of settings corresponding to one of a plurality of operations performed by the vehicle and each setting of the second plurality of settings corresponding to one of a plurality of operators. The controller is configured to adjust at least a position of the support relative to the cab and a position of the mirror relative to the operator cab based on the first setting and the second setting.

In one embodiment, an operator cab assembly for a utility vehicle is disclosed. The utility vehicle including a chassis and an implement that is electively coupled to the chassis. The operator cab assembly includes an operator cab, an operator support positioned within the operator cab and movable relative to the operator cab, and a mirror positioned outwardly relative to the operator cab and movable relative to the operator cab. The operator support and the mirror are each in communication with a control system including a controller. The controller is configured to adjust at least one of a position of the operator support relative to the operator cab and a position of the mirror relative to the operator cab based on an operation being performed by the utility vehicle.

In one embodiment, a control system for use of a utility vehicle is disclosed. The utility vehicle includes a chassis, an operator cab, an operator support supported within and movable relative to the operator cab, and a mirror positioned outwardly and movable relative to the operator cab. The controller system includes a controller configured to receive a first signal corresponding to a first setting of a first plurality of settings, the first plurality of settings corresponding to one of a plurality of operations performed by the vehicle or a plurality of operators that operate the utility vehicle. In response to receiving the first signal from the controller, the controller is further configured to adjust a position of the at least one of the operator support and the mirror.

Before any embodiments of the disclosure are explained in detail, it is to be understood that the disclosure is not limited in its application to the details of construction and the arrangement of components set forth in the following description or illustrated in the following drawings. The disclosure is capable of supporting other embodiments and of being practiced or of being carried out in various ways. Also, it is to be understood that the phraseology and terminology used herein is for the purpose of description and should not be regarded as limiting.

DETAILED DESCRIPTION

Figure 1:
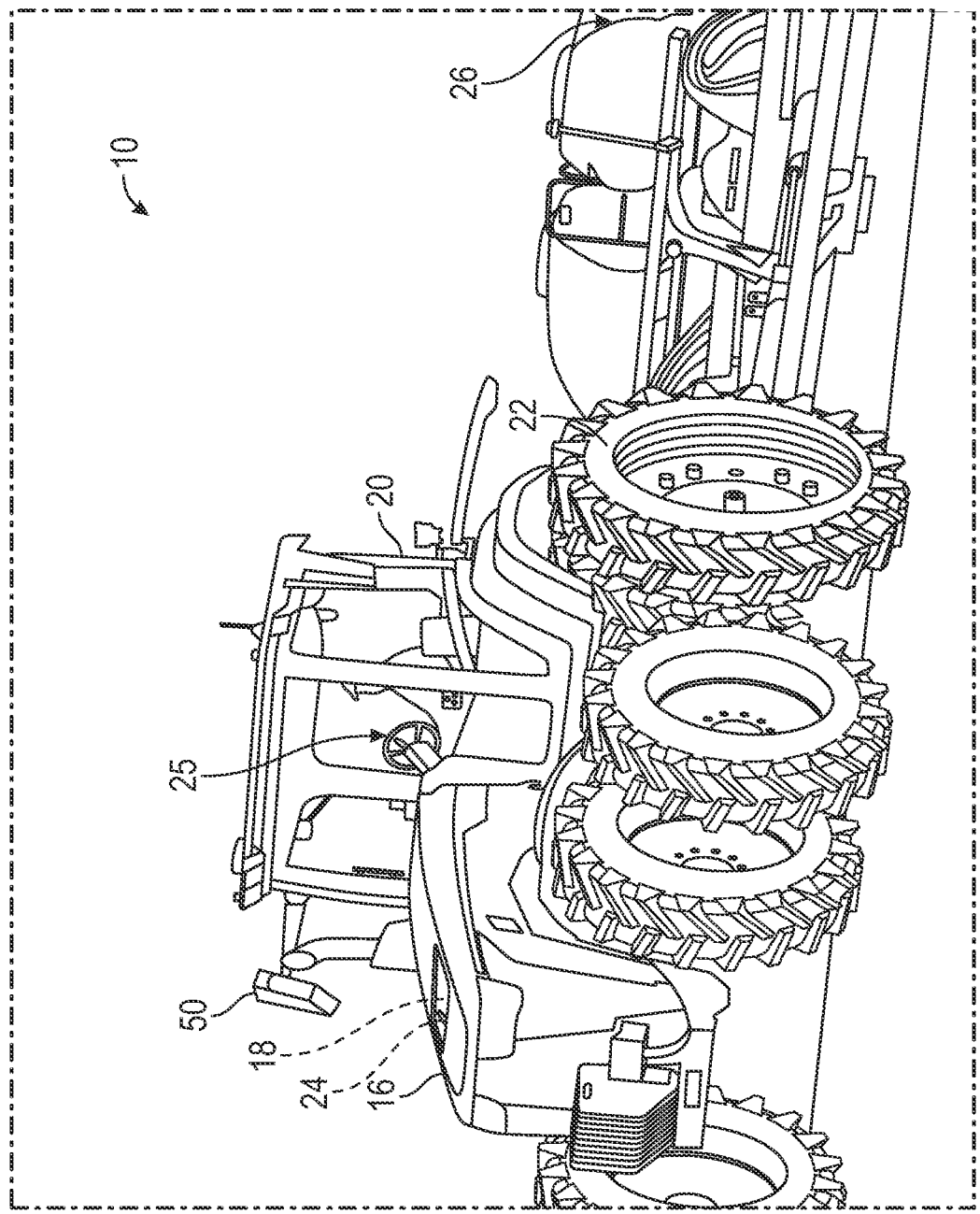
FIG. 1 shows a perspective view of a utility vehicle including an operator cab.

FIG. 1 illustrates a utility vehicle 10. The utility vehicle 10 is in the form of a tractor; however, the utility vehicle 10 may be, for example, a riding lawn mower, harvester, crop sprayer, or other utility vehicle for agricultural, forestry, construction, mining, or other commercial or industrial use. The utility vehicle 10 includes a chassis 16, a prime mover 18, an operator cab 20, a plurality of ground-engaging devices 22, and a control system 24.

The prime mover 18 is configured to move the utility vehicle 10 in a direction of travel via the ground engaging devices 22. The illustrated ground-engaging devices 22 are wheels, but tracks or other suitable ground-engaging devices can be utilized. The chassis 16 supports the prime mover 18 and the control system 24. The prime mover 18 can include an engine, such as a diesel engine, and the control system 24 can include a vehicle control unit (VCU). In the illustrated embodiment, the utility vehicle 10 is coupled to and towing an implement 26 in the form of a planter coupled to a rear of the chassis 16. In other embodiments, the utility vehicle 10 may be coupled to any suitable implement 26 (e.g., a ripper, front end loader, bucket, manure spreaders, planter, tillage, grain cart, bailers, mowers, harvesters, etc.), and the implement may be coupled instead to the front of the chassis 16. Still in other embodiments, more than one implement 26 may be coupled to the chassis 16. For example, a first implement may be coupled to the front of the chassis 16 and a second implement may be coupled to the rear of the chassis.

Figure 2:
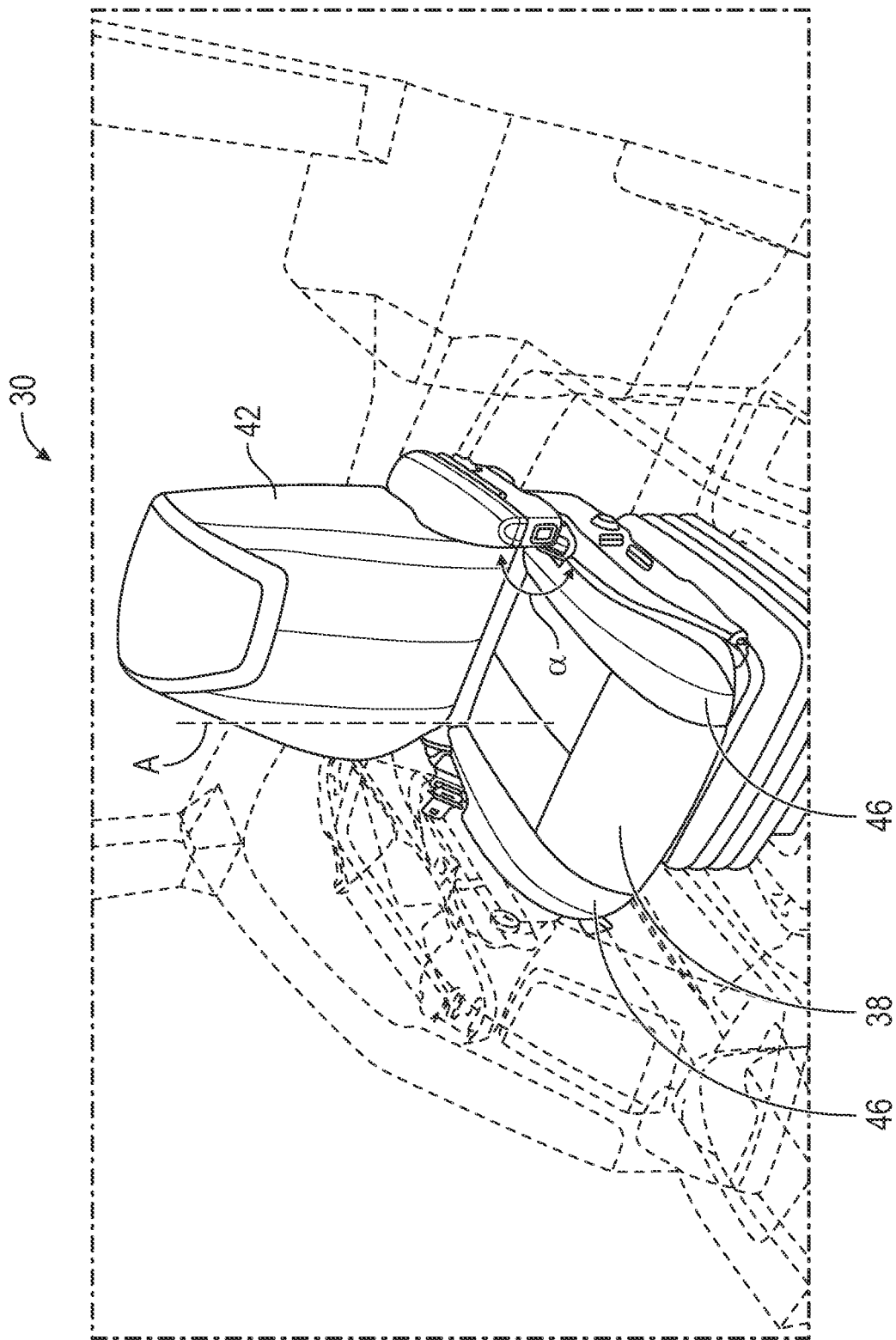
FIG. 2 shows a perspective view of a chair positioned within the cab of the vehicle of FIG. 1.
Figure 3:
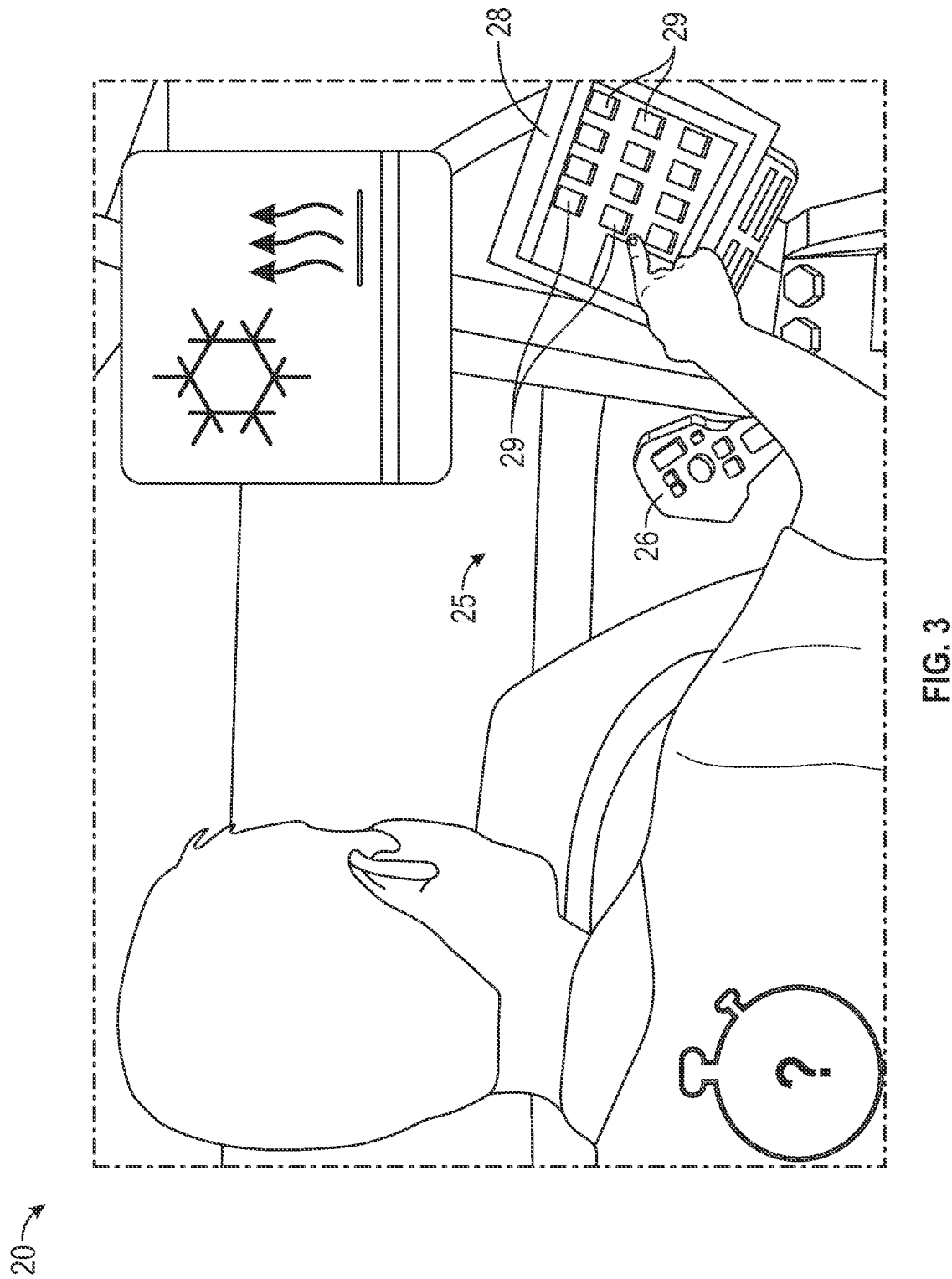
FIG. 3 is a schematic view of a portion of the cab of FIG. 1.

With respect to FIGS. 1-3, the cab 20 includes a vehicle operation system 25 and an operator support 30. The vehicle operation system 25 is positioned in the cab 20 and can include different combinations of input devices. In the illustrated embodiment, the vehicle operation system 25 includes a joystick 26 and a control display 28 (e.g., a touch screen display device having manual actuators 29, FIG. 3). In other embodiments, the vehicle operation system 25 include other or additional input devices, such as a steering wheel, control levers, control pedals, and other suitable input devices.

In the illustrated embodiment, the operator support 30 is a chair. As shown, the chair 30 may include a seat 38 and a backrest 42 coupled to the seat 38 and extending transversely therefrom. The seat 38 and backrest 42 may be made of a number of different materials and both generally include a rigid structure or frame (e.g., metal, rigid plastic, etc.) that provides the general shape and support for the operator, a compressible material such as a foam placed on the frame for cushion, comfort, and ergonomics, and a cover (e.g., nylon, leather, etc.) that holds the compressible material relative to the frame. The seat 38 and/or the backrest 42 may in particular include cushion bolsters 46 that provide lateral support for the operator.

The chair 30 is movable or adjustable relative to the cab 20. In some embodiments, the chair 30 may move or translate forward, rearward, up, and down, and may also be rotatable about an axis A. (FIG. 2) In some embodiments, the backrest 42 is movably or adjustably coupled to the seat 38 to adjust an angle α therebetween. The operator is typically seated in the chair 30 during use and positioned to actuate one or more input devices of the vehicle operation system 25 for purposes of operating movement of the utility vehicle 10 and the attached implement 26.

The cab 20 may also have one or more adjustable mirrors 50 (FIG. 1) extending outwardly therefrom, which are usable to assist the operator in visualizing the area adjacent or surrounding the cab 20 and the utility vehicle 10. The cab 20 may also include a heating, ventilation, and air conditioning (HVAC) system to optionally heat or cool the interior of the cab.

Figure 4:
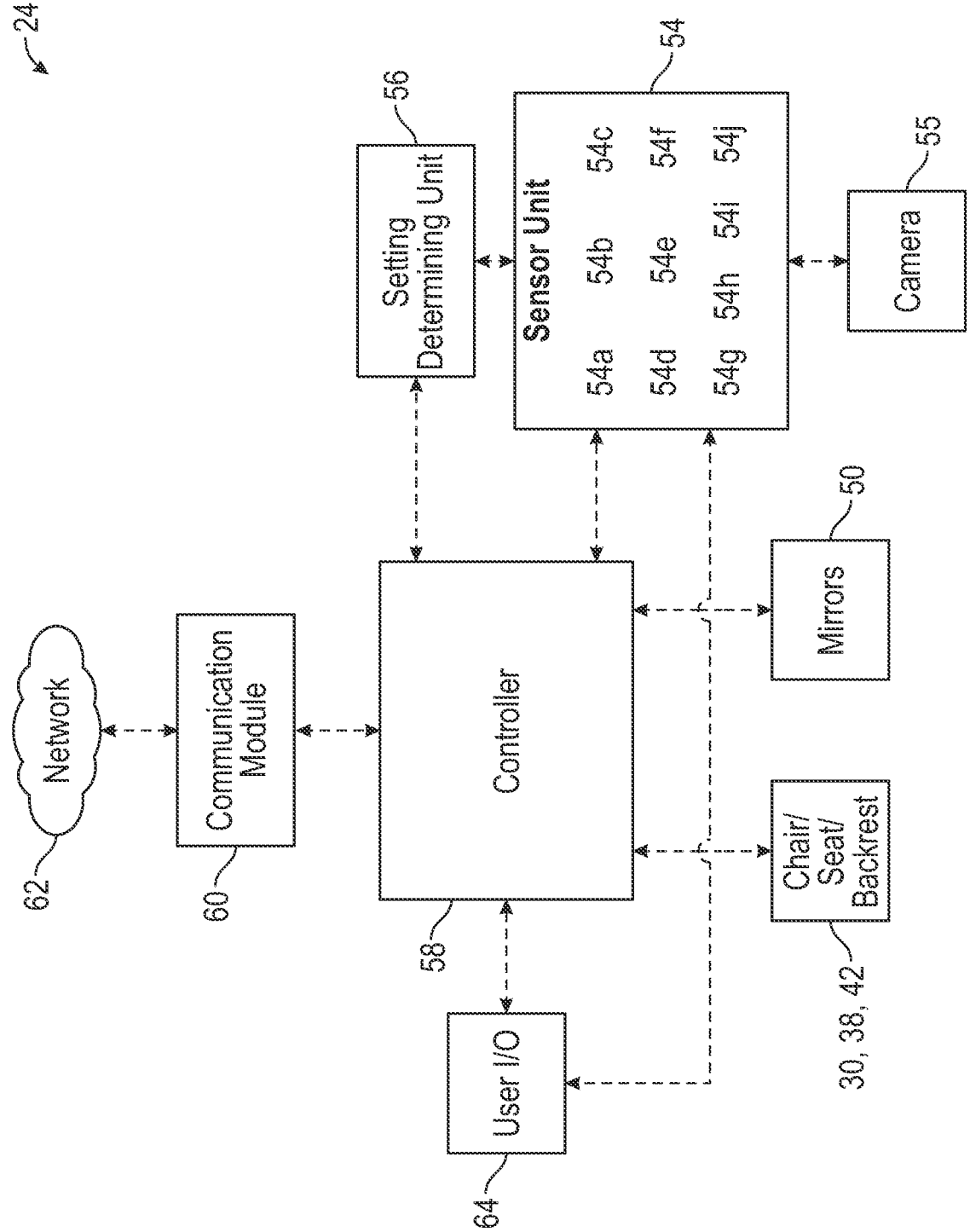
FIG. 4 is a schematic of a control system of the utility vehicle of FIG. 1.

With respect to FIG. 4, a sensor unit 54 including one or more sensors is configured to detect information relating to the utility vehicle and an implement. The one or more sensors may be any suitable type of sensor and configured to detect any suitable type of information. For example, a sensor 54a may detect information relating to a position of the chair 30 relative to the cab 20, a sensor 54b may detect information relating to a position of the backrest 42 relative to the seat 38, a sensor 54c may detect information relating to a position of the mirror(s) 50 relative to the cab 20, a sensor 54d may detect information relating to a type of implement 26 coupled to the chassis 16, a sensor 54e may detect information relating to a location of the implement 26 relative to the chassis 16, a sensor 54f may detect information relating to a position of the implement 26 relative to the chassis 16, a sensor 54g may detect information relating to an operation being performed by the implement 26, a sensor 54h may detect information relating to biometric data (e.g., height, weight, weight distribution relative to the chair, seat, and backrest, etc.) of the operator, a sensor 54i may detect information relating to temperature and/or humidity within the interior of the cab 20, and a sensor 54j may detect information relating to ambient temperature and/or humidity outside of the cab 20, i.e., environmental conditions, among other information. The sensor unit 54 can encompass sensors 54a-54j positioned at any position within the cab 20, external to the cab 20, or otherwise associated with the utility vehicle or implement to detect or record operating or environmental information. For example, the sensor unit 54 may further include or be in communication with one or more cameras 55, lasers, (e.g., for LIDAR or other laser scanning), or scanners.

In some embodiments, a setting determining unit 56, described in greater detail herein, is in communication with the control system 24 and is configured to detect relevant information from the sensor unit 54.

The control system 24 includes a controller 58 with a plurality of inputs and outputs that are operable to receive and transmit information and commands to and from different components, such as the vehicle operation system 25, the sensor unit 54, and the setting determining unit 56. Communication between the controller 58 and the different components can be accomplished through a CAN (e.g., an ISO bus), another communication link (e.g., wireless transceivers), or through a direct connection. The control system 24 further includes a operator input/output module 64 that includes the one or more operator input devices, which are in communication with the controller 58, as well as an output device such as the control display device 28 located in the cab 20. The input/output module 64 may be configured to receive input from the sensor unit 54.

The controller 58 includes memory for storing software, logic, algorithms, programs, a plurality of settings, which include a set of instructions for controlling the chair 30, mirrors 50, and the HVAC, among other components. The controller 58 also includes a processor for carrying out or executing the software, logic, algorithms, programs, set of instructions, etc. stored in the memory.

Often the utility vehicles 10 are operated by multiple operators and are usable for multiple operations. In each instance, settings can be adjusted based on one of the many operations capable of being performed by the utility vehicle. Each time an operator change occurs or an operation change occurs, the seat and mirrors, as well as other components, may need to be reconfigured to accommodate the new occupant and/or operation. The time necessary for each change and reconfiguration over the course of a season or at a specific job site can place a significant burden on productivity or provide a distraction from the task at hand. In some cases an operator may endure a non-ideal setting to avoid the time to readjust.

In an exemplary embodiment, a first plurality of settings and a second plurality of settings are stored in the controller 58. Each setting of the first plurality of settings corresponds to one of a plurality of operations performed by the vehicle 10. The plurality of operations may include operations based on whether or not an implement 26 is coupled to the chassis 16 and what type of implement 26 is coupled to the chassis. In some embodiments, the plurality of operations may also include specific tasks or scenarios that correspond to a respective implement 26. Each of the second plurality of settings corresponds to one operator of a plurality of operators.

In some embodiments, each of the first plurality of settings and each of the second plurality of settings are saved to the controller by a respective operator. In some embodiments, the setting determining unit 56 may be configured to determine or learn (machine learn), via information detected by one or more of the sensors 54a-54j of the sensor unit 54, each of the first plurality of settings and the second plurality of settings from vehicle operations and/or operator habits. In still other embodiments, the controller 58, the setting determining unit 56, or both may be configured to evaluate, via information detected by one or more of the sensors 54a-54j of the sensor unit 54, the position of the chair 30, for example, and determine recommended changes to the position of the chair 30 to individual operators. For example, the controller 58 may be configured to recommend changes to at least one of the position of the chair 30 relative to the operator cab and the position of the backrest 42 relative to the seat 38. Further, the controller 58 may be configured to recommend changes to other components, such as changes to the position of the mirrors 50 relative to the cab 20 based on information detected by the setting determining unit 56.

By way of example, the utility vehicle 10 may be routinely used for pulling a planter (e.g., a first implement) and pulling a grain cart (e.g., a second implement, not shown) and the utility vehicle 10 may be routinely used by two operators (e.g., a first operator and a second operator). A first setting of the first plurality of settings corresponds to use of the planter, and a second setting of the first plurality of settings corresponds to use of the grain cart. Similarly, a first setting of the second plurality of settings corresponds to a first identified operator of the utility vehicle 10, and a second setting of the second plurality of settings corresponds to a second identified operator of the utility vehicle 10.

The controller 58 may be configured to determine (e.g., either via a manual actuator 29 activated by the individual operator in the cab 20 or automatically through the sensor unit 54 or setting determining unit 56) which implement 26 is attached to the chassis 16 to determine and select one of the first or second settings of the first plurality of settings. That is, the controller 58 may be configured to receive a signal corresponding to the operation being performed by the vehicle 10. Specifically, the controller 58 may be configured to receive a first signal corresponding the first setting of the first plurality of settings and a second signal corresponding to the second setting of the first plurality of settings. Similarly, the controller 58 may be configured to determine (e.g., via a manual actuator 29 activated by the individual operator in the cab or automatically through the sensor unit 54 or setting determining unit 56) which operator is in the cab 20 and select one of the first or second settings of the second plurality of settings accordingly. That is, the controller 58 may be configured to receive a signal corresponding to the operator operating the vehicle 10. Specifically, the controller 58 may be configured to receive a third signal corresponding the first setting of the second plurality of settings and a fourth signal corresponding to the second setting of the second plurality of settings. Once the respective settings are determined, the controller 58 is configured send the respective signal to the chair, the one or more mirrors, or both to adjust at least one of a position of the chair 30 relative to the cab 20, a position of the backrest 42 relative to the seat 38, and a position of the one or more mirrors 50 relative to the cab 20 to accommodate the current operation and operator. In some embodiments, the controller 58 may be configured to adjust the HVAC to cool or heat the interior of the cab 20 to a desired temperature based on the chosen or determined settings. As noted above, actuation of one or more manual actuators 29 or sensed information from one or more of the sensors 54a-54j of the sensor unit may generate the respective signals and send the respective signals to the controller 58.

Certain settings are necessary to do a job efficiently and for the operator to attain the comfort needed for long hours in the cab 20. Recalled or automatic setup of stored operably efficient and comfort-based controls of utility vehicle and implement settings saves valuable time on site.

Although the present subject matter has been described in detail with reference to certain embodiments, variations and modifications exist within the scope of one or more independent aspects of the present subject matter, as described.

What is claimed is:
1. A utility vehicle comprising:
    a chassis;
    a prime mover supported by the chassis;
    an operator cab supported by the chassis;
    an operator support positioned within the operator cab and movable relative to the operator cab;
    a mirror positioned outwardly relative to the operator cab and movable relative to the operator cab; and
    a control system including a controller in communication with the operator support and the mirror, the controller configured to select a first setting from a first plurality of settings and a second setting from a second plurality of settings, each setting of the first plurality of settings corresponding to one of a plurality of operations performed by the vehicle and each setting of the second plurality of settings corresponding to one of a plurality of operators,
    wherein the plurality of operations include operations based on a coupling of one or more implements to the chassis and a type of implement coupled to the chassis, and
    wherein the controller is configured to adjust at least one of a position of the support relative to the operator cab or a position of the mirror relative to the operator cab based on the type of implement coupled to the chassis by changing the first setting and the second setting.

2. The utility vehicle of claim 1, further comprising a first actuator in communication with the controller and configured for manual actuation by the operator to select the first setting and a second actuator in communication with the controller and configured for manual actuation by the operator to select the second setting.

3. The utility vehicle of claim 1, further comprising a sensor in communication with the controller, and wherein the controller is configured to detect, via the sensor, when the one or more implements is coupled to the chassis and to select the first setting based on the detection and information relating to the type of implement received from the sensor, wherein the first plurality of settings is different for different implements, and wherein the sensor is one of a sensor configured to detect information relating to a location of the implement relative to the chassis or a sensor configured to detect information relating to a position of the implement relative to the chassis.

4. The utility vehicle of claim 1, further comprising a sensor in communication with the controller, and wherein the controller is configured to detect, via the sensor, biometric data of one of the plurality of operator and to select the second setting based on the detection.

5. The utility vehicle of claim 1, further comprising a setting determining unit in communication with the controller, and wherein the controller is configured to determine a modification to at least the position of the operator support relative to the operator cab and the position of the mirror based on information detected by the setting determining unit.

6. The utility vehicle of claim 5, wherein the setting determining unit includes a camera.

7. The utility vehicle of claim 5, wherein the setting determining unit includes a plurality of biometric sensors.

8. The utility vehicle of claim 1, further comprising a setting determining unit in communication with the controller and configured to machine learn each of the first plurality of settings and each of the second plurality of settings from vehicle operations and operator habits.

9. An operator cab assembly for a utility vehicle, the utility vehicle including a chassis and an implement that is selectively coupled to the chassis, the operator cab assembly comprising:
    an operator cab;
    an operator support positioned within the operator cab and movable relative to the operator cab; and
    a mirror positioned outwardly relative to the operator cab and movable relative to the operator cab;
    wherein the operator support and the mirror are each in communication with a control system including a controller, wherein the controller is configured to receive a first signal corresponding to the operation being performed by the vehicle and a second signal corresponding to the operator operating the utility vehicle, and wherein the controller configured to adjust at least one of a position of the operator support relative to the operator cab or a position of the mirror relative to the operator cab based on a type of implement coupled to the chassis and in response to receiving of the first signal and the second signal.

10. The operator cab assembly of claim 9, wherein the controller is configured to send the first signal to at least one of the operator support and the mirror to adjust the at least one of the position of the operator support relative to the operator cab and the position of the mirror relative to the operator cab.

11. The operator cab assembly of claim 10, wherein the controller is configured to adjust at least one of the position of the operator support relative to the operator cab and the position of the mirror relative to the operator cab based on an operator operating the utility vehicle, and wherein the controller is configured to send the second signal to at least one of the operator support and the mirror to adjust the at least one of the position of the operator support relative to the operator cab and the position of the mirror relative to the operator cab.

12. The operator cab assembly of claim 11, further comprising
a first actuator configured to communicate with the controller, the first actuator configured to generate the first signal upon manual actuation by the operator, the controller configured to receive the first signal in response to the manual actuation of the first actuator by the operator, and
a second actuator configured to communicate with the controller, the second actuator configured to generate the second signal upon manual actuation by the operator, the controller configured to receive the second signal in response to the manual actuation of the second actuator by the operator.

13. The operator cab assembly of claim 11, wherein
the controller is configured to communicate with a sensor, the sensor configured to detect information relating to the type of implement coupled to the chassis to generate the first signal and configured to send the first signal to the controller, and
an actuator is configured to communicate with the controller, the actuator configured to generate the second signal upon manual actuation by the operator, the controller configured to receive the second signal in response to the manual actuation of the actuator by the operator.

14. The operator cab assembly of claim 11, wherein
an actuator is configured to communicate with the controller, the actuator configured to generate the first signal upon manual actuation by the operator, the controller configured to receive the first signal in response to the manual actuation of the actuator by the operator, and
the controller is configured to communicate with a sensor, the sensor configured to detect biometric data of the operator to generate the second signal and configured to send the second signal to the controller.

15. The operator cab assembly of claim 11, further comprising a setting determining unit in communication with the controller and configured to machine learn the at least one of the position of the operator support relative to the operator cab and the position of the mirror relative to the operator cab.

16. A control system for a utility vehicle including a chassis, an operator cab, an operator support supported within and movable relative to the operator cab, and a mirror positioned outwardly and movable relative to the operator cab, the control system comprising:
a controller configured to
receive a first signal corresponding to a first setting of a first plurality of settings, the first plurality of settings corresponding to one of a plurality of operations performed by the utility vehicle or a plurality of operators that operate the utility vehicle, and receive a second signal corresponding to a second setting of a second plurality of settings, the second plurality of settings corresponding to the other of the plurality of operations performed by the vehicle or the plurality of operators, wherein the plurality of operations include operations based on a coupling of an implement to the chassis and a type of the implement coupled to the chassis; and
in response to receiving the first signal and the second signal, adjust a position of the at least one of the operator support and the mirror.

17. The control system of claim 16, wherein the controller is further configured to receive the first signal or the second signal from a sensor configured to detect information relating to a location of the implement relative to the chassis or configured to detect information relating to a position of the implement relative to the chassis.

18. The control system of claim 17, wherein the controller is configured to communicate with a manual actuator that is actuatable to generate at least one of the first signal and the second signal, and wherein the controller is configured to receive the at least one of the first signal and the second signal in response to the manual actuator being actuated by the operator.

19. The control system of claim 17, wherein the controller is configured to communicate with a sensor configured to detect when the implement is coupled to the chassis to generate at least one of the first signal and the second signal, and wherein the controller is configured to receive the at least one of the first signal and the second signal from the sensor.

20. The control system of claim 17, wherein the controller is configured to communicate with a sensor configured to detect biometric data of one of the plurality of operators to generate at least one of the first signal and the second signal, and wherein the controller is configured to receive the at least one of the first signal and the second signal from the sensor.

* * * * *